US012766201B2

(12) United States Patent
Kjaer et al.

(10) Patent No.: US 12,766,201 B2
(45) Date of Patent: Oct. 20, 2026

(54) UROKINASE PLASMINOGEN ACTIVATOR RECEPTOR TARGETED RADIOLABELED PEPTIDE CONJUGATES

(71) Applicant: CURASIGHT A/S, Copenhagen N (DK)

(72) Inventors: Andreas Kjaer, Frederiksberg (DK); Knud Jorgen Jensen, Copenhagen (DK); Jakob Madsen, Skovlunde (DK); Troels Elmer Jeppesen, Copenhagn (DK)

(73) Assignee: CURASIGHT A/S, Copenhagen N (DK)

(*) Notice: Subject to any disclaimer, the term of this patent is extended or adjusted under 35 U.S.C. 154(b) by 666 days.

(21) Appl. No.: 18/039,542

(22) PCT Filed: Nov. 26, 2021

(86) PCT No.: PCT/EP2021/083154
§ 371 (c)(1),
(2) Date: May 31, 2023

(87) PCT Pub. No.: WO2022/117454
PCT Pub. Date: Jun. 9, 2022

(65) Prior Publication Data

US 2024/0009331 A1 Jan. 11, 2024

(30) Foreign Application Priority Data

Dec. 1, 2020 (SE) .................................... 2051401-4

(51) Int. Cl.
*A61K 51/08* (2006.01)

(52) U.S. Cl.
CPC .................................. *A61K 51/088* (2013.01)

(58) Field of Classification Search
None
See application file for complete search history.

(56) References Cited

U.S. PATENT DOCUMENTS

| | | | | |
|---|---|---|---|---|
| 8,568,689 | B1 * | 10/2013 | Cuthbertson ...... | A61K 49/0056 424/9.1 |
| 2009/0087377 | A1 | 4/2009 | Azhdarinia et al. | |
| 2012/0053318 | A1 | 3/2012 | Simms et al. | |

FOREIGN PATENT DOCUMENTS

| | | | |
|---|---|---|---|
| CN | 107652358 | A | 2/2018 |
| WO | WO-2006/036071 | A2 | 4/2006 |
| WO | WO-2006/036071 | A3 | 4/2006 |
| WO | WO-2010/015668 | A1 | 2/2010 |
| WO | WO-2011015649 | A1 | 2/2011 |
| WO | WO-2011/101261 | A2 | 8/2011 |
| WO | WO-2011/101261 | A3 | 8/2011 |
| WO | WO-2013/167130 | A1 | 11/2013 |
| WO | WO-2014/086364 | A1 | 6/2014 |
| WO | WO-2016/041558 | A1 | 3/2016 |
| WO | WO-2017/023994 | A1 | 2/2017 |
| WO | WO-2017/192605 | A1 | 11/2017 |

OTHER PUBLICATIONS

Zhang, Xin et al., "Imaging of human pancreatic cancer xenografts by single-photon emission computed tomography with 99mTc-Hynic-PEG-AE105", Oncology Letters, vol. 10, No. 4, Oct. 17, 2015 (Oct. 17, 2015), pp. 2253-2258.

Loft Mathias Dyrberg et al., "Improved positron emission tomography imaging of glioblastoma cancer using novel168Ga-labeled peptides targeting the urokinase-type plasminogen activator receptor (uPAR)", Amino Acids (2017) 49:1089-1100.

Knor, et al., "Development and evaluation of peptidic ligands targeting tumour-associated urokinase plasminogen activator receptor (uPAR) for use in a-emitter therapy for disseminated ovarian cancer", Eur J Nucl Med Mol Imaging (2008) 35:53-64.

Swedish Search Report for Application No. 2051401-4 filed Jul. 20, 2021.

International Search Report for PCT Application PCT/EP2021/083154 dated Mar. 1, 2022.

Persson, et al., "Quantitative PET of Human Urokinase-Type Plasminogen Activator Receptor with $^{64}$Cu-DOTA-AE105: Implications for Visualizing Cancer Invasion", The Journal of Nuclear Medicine, vol. 53, No. 1, Jan. 2012, 8 pages.

* cited by examiner

*Primary Examiner* — Celeste A Roney
(74) *Attorney, Agent, or Firm* — MOSER TABOADA

(57) ABSTRACT

The present invention describes Urokinase Plasminogen Activator Receptor (uPAR) targeted radiolabeled conjugates suited for non-invasive PET imaging, SPECT imaging or targeted radionuclide therapy. In particular, but not limited to, the invention related to imaging and therapy of cancer diseases.

33 Claims, 1 Drawing Sheet

Specification includes a Sequence Listing.

SEQUENCE LISTING

<160> NUMBER OF SEQ ID NOS: 7

<210> SEQ ID NO 1
<211> LENGTH: 9
<212> TYPE: PRT
<213> ORGANISM: Artificial Sequence
<220> FEATURE:
<223> OTHER INFORMATION: Laboratory Synthesized, name of sequence is AE105
<220> FEATURE:
<221> NAME/KEY: SITE
<222> LOCATION: (2)..(2)
<223> OTHER INFORMATION: Cha (3-Cyclohexyl-D-alanine) (CAS No. 213178-94-0)
<220> FEATURE:
<221> NAME/KEY: SITE
<222> LOCATION: (4)..(4)
<223> OTHER INFORMATION: D-Ser
<220> FEATURE:
<221> NAME/KEY: SITE
<222> LOCATION: (5)..(5)
<223> OTHER INFORMATION: D-Arg

<400> SEQUENCE: 1

```
Asp Xaa Phe Ser Arg Tyr Leu Trp Ser
1   5
```

<210> SEQ ID NO 2
<211> LENGTH: 13
<212> TYPE: PRT
<213> ORGANISM: Artificial Sequence
<220> FEATURE:
<223> OTHER INFORMATION: Laboratory Synthesized, name of sequence is AE344
<220> FEATURE:
<221> NAME/KEY: SITE
<222> LOCATION: (3)..(3)
<223> OTHER INFORMATION: O2Oc (2-(2-(2-aminoethoxy)ethoxy)acetic acid) (CAS No. 134978-97-5)
<220> FEATURE:
<221> NAME/KEY: SITE
<222> LOCATION: (4)..(4)
<223> OTHER INFORMATION: O2Oc (2-(2-(2-aminoethoxy)ethoxy)acetic acid) (CAS No. 134978-97-5)
<220> FEATURE:
<221> NAME/KEY: SITE
<222> LOCATION: (6)..(6)
<223> OTHER INFORMATION: Cha (3-Cyclohexyl-D-alanine) (CAS No. 213178-94-0)
<220> FEATURE:
<221> NAME/KEY: SITE
<222> LOCATION: (8)..(8)
<223> OTHER INFORMATION: D-Ser
<220> FEATURE:
<221> NAME/KEY: SITE
<222> LOCATION: (9)..(9)
<223> OTHER INFORMATION: D-Arg

<400> SEQUENCE: 2

```
Glu Glu Xaa Xaa Asp Xaa Phe Ser Arg Tyr Leu Trp Ser
1               5                   10
```

<210> SEQ ID NO 3
<211> LENGTH: 13
<212> TYPE: PRT
<213> ORGANISM: Artificial Sequence
<220> FEATURE:
<223> OTHER INFORMATION: Laboratory Synthesized, name of sequence is AE345
<220> FEATURE:
<221> NAME/KEY: SITE
<222> LOCATION: (3)..(3)
<223> OTHER INFORMATION: O2Oc (2-(2-(2-aminoethoxy)ethoxy)acetic acid) (CAS No. 134978-97-5)

```
<220> FEATURE:
<221> NAME/KEY: SITE
<222> LOCATION: (4)..(4)
<223> OTHER INFORMATION: O2Oc (2-(2-(2-aminoethoxy)ethoxy)acetic acid)
      (CAS No. 134978-97-5)
<220> FEATURE:
<221> NAME/KEY: SITE
<222> LOCATION: (6)..(6)
<223> OTHER INFORMATION: Cha (3-Cyclohexyl-D-alanine) (CAS No. 213178-
      94-0)
<220> FEATURE:
<221> NAME/KEY: SITE
<222> LOCATION: (8)..(8)
<223> OTHER INFORMATION: D-Ser
<220> FEATURE:
<221> NAME/KEY: SITE
<222> LOCATION: (9)..(9)
<223> OTHER INFORMATION: D-Arg
<220> FEATURE:
<221> NAME/KEY: AMIDATION
<222> LOCATION: (13)..(13)
<223> OTHER INFORMATION: Amidation of the C-terminal Serine residue

<400> SEQUENCE: 3

Glu Glu Xaa Xaa Asp Xaa Phe Ser Arg Tyr Leu Trp Ser
1               5                   10


<210> SEQ ID NO 4
<211> LENGTH: 11
<212> TYPE: PRT
<213> ORGANISM: Artificial Sequence
<220> FEATURE:
<223> OTHER INFORMATION: Laboratory Synthesized, name of sequence is
      AE346
<220> FEATURE:
<221> NAME/KEY: SITE
<222> LOCATION: (1)..(1)
<223> OTHER INFORMATION: O2Oc (2-(2-(2-aminoethoxy)ethoxy)acetic acid)
      (CAS No. 134978-97-5)
<220> FEATURE:
<221> NAME/KEY: SITE
<222> LOCATION: (2)..(2)
<223> OTHER INFORMATION: O2Oc (2-(2-(2-aminoethoxy)ethoxy)acetic acid)
      (CAS No. 134978-97-5)
<220> FEATURE:
<221> NAME/KEY: SITE
<222> LOCATION: (4)..(4)
<223> OTHER INFORMATION: Cha (3-Cyclohexyl-D-alanine) (CAS No. 213178-
      94-0)
<220> FEATURE:
<221> NAME/KEY: SITE
<222> LOCATION: (6)..(6)
<223> OTHER INFORMATION: D-Ser
<220> FEATURE:
<221> NAME/KEY: SITE
<222> LOCATION: (7)..(7)
<223> OTHER INFORMATION: D-Arg

<400> SEQUENCE: 4

Xaa Xaa Asp Xaa Phe Ser Arg Tyr Leu Trp Ser
1               5                   10


<210> SEQ ID NO 5
<211> LENGTH: 12
<212> TYPE: PRT
<213> ORGANISM: Artificial Sequence
<220> FEATURE:
<223> OTHER INFORMATION: Laboratory Synthesized, name of sequence is
      AE347
<220> FEATURE:
<221> NAME/KEY: SITE
<222> LOCATION: (3)..(3)
<223> OTHER INFORMATION: O2Oc (2-(2-(2-aminoethoxy)ethoxy)acetic acid)
      (CAS No. 134978-97-5)
<220> FEATURE:
```

```
<221> NAME/KEY: SITE
<222> LOCATION: (5)..(5)
<223> OTHER INFORMATION: Cha (3-Cyclohexyl-D-alanine) (CAS No. 213178-
      94-0)
<220> FEATURE:
<221> NAME/KEY: SITE
<222> LOCATION: (7)..(7)
<223> OTHER INFORMATION: D-Ser
<220> FEATURE:
<221> NAME/KEY: SITE
<222> LOCATION: (8)..(8)
<223> OTHER INFORMATION: D-Arg
<220> FEATURE:
<221> NAME/KEY: AMIDATION
<222> LOCATION: (12)..(12)
<223> OTHER INFORMATION: Amidation of the C-terminal Serine residue

<400> SEQUENCE: 5

Glu Glu Xaa Asp Xaa Phe Ser Arg Tyr Leu Trp Ser
1               5                   10


<210> SEQ ID NO 6
<211> LENGTH: 11
<212> TYPE: PRT
<213> ORGANISM: Artificial Sequence
<220> FEATURE:
<223> OTHER INFORMATION: Laboratory Synthesized, name of sequence is
      AE348
<220> FEATURE:
<221> NAME/KEY: SITE
<222> LOCATION: (2)..(2)
<223> OTHER INFORMATION: O2Oc (2-(2-(2-aminoethoxy)ethoxy)acetic acid)
      (CAS No. 134978-97-5)
<220> FEATURE:
<221> NAME/KEY: SITE
<222> LOCATION: (4)..(4)
<223> OTHER INFORMATION: Cha (3-Cyclohexyl-D-alanine) (CAS No. 213178-
      94-0)
<220> FEATURE:
<221> NAME/KEY: SITE
<222> LOCATION: (6)..(6)
<223> OTHER INFORMATION: D-Ser
<220> FEATURE:
<221> NAME/KEY: SITE
<222> LOCATION: (7)..(7)
<223> OTHER INFORMATION: D-Arg
<220> FEATURE:
<221> NAME/KEY: AMIDATION
<222> LOCATION: (11)..(11)
<223> OTHER INFORMATION: Amidation of the C-terminal Serine residue

<400> SEQUENCE: 6

Glu Xaa Asp Xaa Phe Ser Arg Tyr Leu Trp Ser
1               5                   10


<210> SEQ ID NO 7
<211> LENGTH: 11
<212> TYPE: PRT
<213> ORGANISM: Artificial Sequence
<220> FEATURE:
<223> OTHER INFORMATION: Laboratory Synthesized, name of sequence is
      AE349
<220> FEATURE:
<221> NAME/KEY: SITE
<222> LOCATION: (4)..(4)
<223> OTHER INFORMATION: Cha (3-Cyclohexyl-D-alanine) (CAS No. 213178-
      94-0)
<220> FEATURE:
<221> NAME/KEY: SITE
<222> LOCATION: (6)..(6)
<223> OTHER INFORMATION: D-Ser
<220> FEATURE:
<221> NAME/KEY: SITE
<222> LOCATION: (7)..(7)
<223> OTHER INFORMATION: D-Arg
```

-continued

```
<400> SEQUENCE: 7

Glu Glu Asp Xaa Phe Ser Arg Tyr Leu Trp Ser
1               5                   10
```

UROKINASE PLASMINOGEN ACTIVATOR RECEPTOR TARGETED RADIOLABELED PEPTIDE CONJUGATES

FIELD OF THE INVENTION

The present invention relates to Urokinase Plasminogen Activator Receptor (uPAR) targeted radiolabeled conjugates suited for non-invasive PET imaging, SPECT imaging or targeted radionuclide therapy. In particular, but not limited to, the invention related to imaging and therapy of cancer diseases.

TECHNICAL BACKGROUND

Urokinase-type plasminogen activator receptor (uPAR) is over-expressed in a variety of human cancers whereas the expression in non-cancer tissue is low. Accordingly, uPAR is an attractive imaging target for diagnosis, staging, risk stratification, treatment monitoring and tailoring therapy in cancer patients.

Malignant tumors are capable of degrading the surrounding extracellular matrix, resulting in local invasion or metastasis. Urokinase-type plasminogen activator (uPA) and its cell surface receptor (uPAR) are central molecules for cell surface-associated plasminogen activation both in vitro and in vivo. High expression of uPA and uPAR in many types of human cancers correlate with malignant tumor growth and associate with a poor prognosis, possibly indicating a causal role for the uPA/uPAR system in cancer progression and metastasis. Studies by immunohistochemistry and in situ hybridization indicate that expression levels of the components from the uPA/uPAR system are generally very low in normal tissues and benign lesions. It has also been reported that the uPA/uPAR system is involved in regulating cell-extracellular matrix interactions by acting as an adhesion receptor for vitronectin and by modulating integrin function. Based on these properties, the uPA/uPAR system is consequently considered an attractive target for cancer therapy.

uPAR-PET has previously been performed successfully in humans using [$^{64}$Cu]Cu-DOTA-AE105 (Persson M, Skovgaard D, Brandt-Larsen M, Christensen C, Madsen J, Nielsen C H, Thurison T, Klausen T L, Holm S, Loft A, Berthelsen A K, Ploug M, Pappot H, Brasso K, Kroman N, Højgaard L, Kjaer A. First-in-human uPAR PET: Imaging of Cancer Aggressiveness. Theranostics. 2015 Sep. 13; 5(12): 1303-16. doi: 10.7150/thno.12956. eCollection 2015. PubMed PMID: 26516369; PubMed Central PMCID: PMC4615734.) and [$^{68}$Ga]Ga-NOTA-AE105 (Skovgaard D, Persson M, Brandt-Larsen M, Christensen C, Madsen J, Klausen T L, Holm S, Andersen F L, Loft A, Berthelsen A K, Pappot H, Brasso K, Kroman N, Hrøjgaard L, Kjaer A. Safety, Dosimetry, and Tumor Detection Ability of (68)Ga-NOTA-AE105: First-in-Human Study of a Novel Radioligand for uPAR PET Imaging. J Nucl Med. 2017 March; 58(3):379-386. doi: 10.2967/jnumed.116.178970. Epub 2016 Sep. 8. PubMed PMID: 27609788.) for detection of cancers.

Targeted radionuclide therapy using [$^{177}$Lu]Lu-DOTA-AE105 has previously been performed successfully in human xenograft tumors (colorectal cancer and metastatic prostate cancer) implanted in nude mice (Persson M, Juhl K, Rasmussen P, Brandt-Larsen M, Madsen J, Ploug M, Kjaer A. uPAR targeted radionuclide therapy with (177)Lu-DOTA-AE105 inhibits dissemination of metastatic prostate cancer. Mol Pharm. 2014 Aug. 4; 11(8):2796-806. doi: 10.1021/mp500177c. Epub 2014 Jul. 1. PubMed PMID: 24955765. and Persson M, Rasmussen P, Madsen J, Ploug M, Kjaer A. New peptide receptor radionuclide therapy of invasive cancer cells: in vivo studies using 177Lu-DOTA-AE105 targeting uPAR in human colorectal cancer xenografts. Nucl Med Biol. 2012 October; 39(7):962-9. doi: 10.1016/j.nucmedbio. 2012.05.007. Epub 2012 Jun. 26. PubMed PMID: 22739362.).

Having shown the feasibility of uPAR-PET imaging and uPAR-targeted radionuclide therapy, the current invention relates to surprisingly improved characteristics of second generation uPAR-targeted peptide ligands based on novel modified peptides. These improved characteristics relate to, but are not limited to solubility, hydrophilicity, biodistribution and high uptake in tumors.

SUMMARY OF THE INVENTION

The present invention refers to a urokinase Plasminogen Activator Receptor (uPAR)-targeting peptide conjugate comprising:

- a radionuclide coupled via a chelating agent or covalently to a peptide binding to uPAR; and
- a linker group, wherein the peptide binding to uPAR and the linker group is connected by covalent bonds, wherein the linker group comprises oligoethylene glycols or other short oligomers such as oligo-glycerol, oligo-lactic acid or carbohydrates which are optionally connected by covalent bonds to at least one amino acid. According to one specific embodiment, the linker group is an oligoethylene glycol, which is of special interest according to the present invention.

As should be understood from above, according to the present invention the peptide is linked to a radionuclide covalently or via a chelator (chelating agent). This further implies that the present invention also embodies a peptide conjugate built on radionucleotide-chelator-linker-peptide. Moreover, also alternatives without a chelator, i.e. built on radionucleotide-linker-peptide, are part of the present invention.

The concept according to the present invention differs in relation to known uPAR-targeting peptide conjugates in several ways. As an example, in WO2006/036071 there is disclosed contrast agents for detection of uPAR, especially contrast agents comprising a peptidic vector binding to uPAR, labelled with an imageable moiety. It should be noted that the contrast agents disclosed in WO2006/036071 does not include a peptide sequence with only 1 amino acid between the linker and the essential Phe in the structure, which also implies that the peptides used have not been synthesized with only one amino acid between the linker and the Phe. This is an important difference in comparison to the present invention. By use of a linker group as specified above, according to the present invention, there is obtained enhanced binding. This is a very surprising effect as this is not obvious when incorporating a linker in the composition. The use of a linker group comprising oligoethylene glycols or other short oligomers such as oligo-glycerol, oligo-lactic acid or carbohydrates, such as specified above, as provided according to the present invention provides for enhanced binding. One possible reason to this may be based on the better solubility in water and thus easier access to the receptor. Moreover, an entropic effect may be in play and the linker according to the present invention might be stabilizing the binding and increasing the off-rate.

Based on the above, the incorporation of a linker and the linker type giving an enhanced binding according to the present invention is an important difference when comparing the present invention with the compositions according to WO2006/036071. Moreover, it should also be noted that WO2006/036071 is not directed to the core intended usage according to the present invention. For instance, WO2006/036071 is not directed to therapy or radionucleotide therapy. As such, the core of WO2006/036071 is directed to imaging contrast, but not therapy where radionucleotides are involved.

Furthermore, in WO2013/167130 there is disclosed a 177-Lu labelled peptide for site-specific targeting of the Urokinase Plasminogen Activator Receptor (uPAR) thereby enabling treatment of a cancer disease associated with high uPAR expression; e.g. treatment of colorectal cancer by administering to a patient an effective amount of the 177-Lu labelled peptide. In this case the peptide sequence does not include linkers, which according to the present invention, surprisingly, enhances the binding. Again, a linker and especially the oligo-linker type according to the present invention is not involved in the compositions mentioned in WO2013/167130.

It may further be mentioned that these differences mentioned above are also true when comparing the present invention with e.g. the articles mentioned above.

Moreover, and to summarize, the linker type according to the present invention provides for enhanced binding. Other potential benefits are an increase of the uptake in vivo in certain cases, a slower off-rate and thus a longer binding time to the receptor, which in turn may provide a higher radiation dose to the cancer being treated.

In this regard it may also be mentioned that the concept of providing a radionucleotide coupled via a chelating agent or covalently to a peptide binding to uPAR, such as according to the present invention, is not the taught direction of any of the documents mentioned above.

Furthermore, there are also other differences, such as the peptides involved according to certain specific embodiments, etc. This is further developed in the description below.

SPECIFIC EMBODIMENTS OF THE INVENTION

Below some specific embodiments of the present invention are presented and discussed further.

According to one embodiment of the present invention, the linker group comprises oligoethylene glycols or other short oligomers such as oligo-glycerol, oligo-lactic acid or carbohydrates which are optionally connected by covalent bonds to at least one amino acid. As an example, Glu or Asp may be such amino acids used. Also short peptide sequences may be incorporated.

Again, this type of linker groups part of the present invention is not intended or used in the prior art documents mentioned above.

In one embodiment of the present invention, the linker group comprises oligoethylene glycols, which are connected by covalent bonds to at least one amino acid, wherein the at least one amino acid may be covalently linked to another amino acid forming a peptide bond and thus may form an oligopeptide. Thus, in one embodiment of the present invention the linker group comprises oligoethylene glycols which are connected by covalent bonds to at least an oligopeptide. Accordingly, the linker group may be a hydrophilic linker group. Furthermore, the at least one amino acid may be selected from proteinogenic amino acids and non-proteinogenic amino acids, which includes natural amino acids and synthetic amino acids. In relation to this, it may further be mentioned that the natural amino acids may include C-alpha alkylated amino acids such aminoisobutyric acid (Aib), N-alkylated amino acids such as sarcosine, and naturally occurring beta-amino acids such as beta-alanine. Further, the synthetic amino acids may include amino acids with non-proteinogenic side-chains such as cyclohexyl alanine, gamma-amino acids, and dipeptide mimics. The term dipeptide mimics may be interpreted as an organic molecule that mimics a dipeptide by displaying the two amino acid side-chains, e.g., having a reduced amide bond linking two residues together. Amino acids with non-proteinogenic side-chains may also include amino acids with side-chains with restricted motion in chi-space. The term restricted motion in chi-space may be interpreted as restricted flexibility in the rotation of the side-chain groups. The oligopeptides may consist of up to fifty amino acids and may include dipeptides, tripeptides, tetrapeptides, and pentapeptides, and may further be made up by proteinogenic amino acids and non-proteinogenic amino acids.

According to one specific embodiment of the present invention, the linker group is -Glu-Glu-NH—$CH_2$—$CH_2$—O—$CH_2$—$CH_2$—O—$CH_2$—CO—NH—$CH_2$—$CH_2$—O—$CH_2$—$CH_2$—O—$CH_2$—CO—. Where the term O2Oc is used throughout the present application it means the chemical entity —NH—$CH_2$—$CH_2$—O—$CH_2$—$CH_2$—O—$CH_2$—CO—. Hence, O2Oc—O2Oc means —NH—$CH_2$—$CH_2$—O—$CH_2$—$CH_2$—O—$CH_2$—CO—NH—$CH_2$—$CH_2$—O—$CH_2$—$CH_2$—O—$CH_2$—CO—. Further, the present invention is not limited to the ethylene glycol units being connected by amide bonds, in fact each ethylene unit can be linked by either an ether or an amide, or in principle other covalent bonds. The ethylene glycol chains may have varying length, i.e. the number of repeating units may be in the range of n=1-10, where n is the number of repeating units in a linker corresponding to —$(CH_2—CH_2—O)_n$—. Further, the amino acids in the linker are not limited to glutamic acid (Glu), other combinations of amino acids with acidic side-chains i.e. aspartic acid, may be included, such as Asp-Asp, Glu-Asp or Asp-Glu. Further, it could also be combinations of other hydrophilic amino acids, i.e. combinations of for example, serine (Ser), Threonine (Thr), histidine (His) or lysine (Lys).

In another embodiment of the present invention, the receptor binding peptide may be selected from the group consisting of:

```
-Asp-Cha-Phe-ser-arg-Tyr-Leu-Trp-Ser;
and

-Asp-Cha-Phe-ser-arg-Tyr-Leu-Trp-Ser-NH2.
```

Furthermore, the covalent bonds of the present invention may be selected from the group consisting of an amide, a carbamate, thiourea, an ester, ether, amine, a triazole or any other covalent bond commonly used to couple chemical moieties by solid-phase synthesis.

In another embodiment of the present invention the uPAR-targeting peptide conjugate has a uPAR-binding affinity less than 100 nM, preferably less than 50 nM, preferably less than 25 nM.

Furthermore, the conjugate according to the present invention may be used in different fields. Moreover, different radionucleotides are more interesting according to the present invention for different applications.

According to one embodiment, the radionuclide is for PET imaging, in particular selected from the following isotopes 11C, 18F, 13N, 150, 44Sc, 52gMn, 60Cu, 61Cu, 62Cu, 64Cu, 68Ga, 76Br, 82Rb, 86Y, 89Zr, 94mTc, 124I, preferably selected from 18F, 64Cu, 68Ga, 89Zr. According to yet another specific embodiment of the present invention, the radionuclide is for SPECT imaging, in particular selected from the following isotopes 67Ga, 111In, 123I, 125I, 131I, 99mTc, preferably selected from 99mTc, 111In, 123I. Moreover, according to yet another specific embodiment, the radionuclide is for targeted radionuclide therapy (alpha, beta-emitters or auger), preferably selected from the following isotopes 67Cu, 177Lu, 89Sr, 90Y, 117mSn, 131I, 153Sm, 166Ho, 186Re, 188Re, 211At, 212Pb, 212Bi, 213Bi, 223Ra, 224Ra, 225Ac, 227Th, more preferably selected from 67Cu, 90Y, 177Lu, 211At, 225Ac, 227Th.

Furthermore, also the chelating agent may be of different type. According to one specific embodiment of the present invention, the chelating agent is selected from any of DOTA, CB-DO2A, 3p-C-DEPA, TCMC, Oxo-DO3A, TETA, TE2A, CB-TE2A, CB-TE1A1P, CB-TE2P, MM-TE2A, DM-TE2A, SarAr, SarAr-NCS, diamSar, AmBaSar, BaBaSar, ATSM, CB-TE1A1P and CB-TE2P, NOTA, NETA, TACN-TM, NODAGA, TRAP, AAZTA, DATA, $H_2$dedpa, CP256, PCTA, THP, DTPA, 1B4M-DTPA, CHX-A"-DTPA, TRAP (PRP9), NOPO, DFO HOPO, H6phospa, PCTA, $H_2$dedpa, $H_4$octapa, $H_2$azapa, $H_5$decapa, HBED, HBED-cc, SHBED, BPCA, CP256, HEHA, PEPA and RESCA1, preferably from any of DOTA, NOTA, CB-TE2A, NODAGA, DFO, HBED, HBED-cc.

As hinted, the uPAR-targeting peptide conjugate according to the present invention may be used in the treatment of a disease or in diagnosis of a disease.

In one embodiment of the present invention, the disease may be selected from the group consisting of cancer and inflammatory diseases. Further, since uPAR is a well-known cancer target highly expressed in GBMs and several other cancers, the cancers that are targeted by the present invention may be GBM, including other brain cancers (incl. central and peripheral nervous system), breast cancer, head and neck squamous cell carcinoma and other head and neck cancers (e.g. lip, oral cavity, larynx, nasopharynx, oropharynx, hypopharynx cancers), renal cell carcinoma, lung cancer, colorectum, prostate, stomach, liver, thyroid, bladder, esophagus, pancreas, kidney, corpus uteri, cervix uteri, melanoma, ovary, gallbladder, multiple myeloma, testis, vulva, salivary glands, mesothelioma, penis, kaposi sarcoma, vagina, neuroendocrine tumors and neuroendocrine carcinomas.

In one embodiment of the present invention the cancer may be selected from the group consisting of gliomas, glioblastomas or other brain tumors, pancreatic cancer, head-and-neck cancer, breast cancer, lung cancer, colorectal cancer, esophageal cancer, gastric cancer, liver cancer, neuroendocrine tumors, neuroendocrine carcinomas, prostate cancer.

In one embodiment of the present invention the cancer is selected from the group consisting of gliomas, glioblastomas, pancreatic cancer, head-and-neck cancer, colorectal cancer, lung cancer and breast cancer. Further, in one specific embodiment of the present invention the cancer is gliomas or glioblastomas. In another specific embodiment of the present invention the cancer is pancreatic cancer. In even a further specific embodiment of the present invention the cancer is breast cancer.

Moreover, also selectivity for cancer tissue is of interest in relation to the present invention. According to one specific embodiment of the present invention, the receptor-targeting conjugate has a selectivity for cancer tissue of at least 60%, preferably above 70%, more preferably above 80% and most preferably above 90%. Thus, the conjugate product is characterized by having a selectivity for cancer tissue on preferred at least 60%, or 70% or 80%, or 90%.

In another embodiment of the present invention the inflammatory diseases are selected from the group consisting of arthritis and atherosclerosis.

Furthermore, the present invention also refers to a pharmaceutical composition for use according to the present invention, wherein the disease is selected from the group consisting of cancer and inflammatory diseases. Alternative of diseases are provided above, such as cancer types, arthritis or atherosclerosis.

DETAILED DESCRIPTION OF THE DRAWINGS AND EXAMPLES

Although individual features may be included in different embodiments, these may possibly be combined in other ways, and the inclusion in different embodiments does not imply that a combination of features is not feasible. In addition, singular references do not exclude a plurality. In the context of the present invention, the terms "a", "an" does not preclude a plurality.

The term "conjugate" means two or more molecules, such as a peptide and a linker and radionuclide, attached to each other by covalent bonds and/or chelation.

SPR Experiments

Covalent immobilization of purified human proUPA$^{S356A}$ was accomplished by injecting 12.5 μg/ml protein dissolved in 10 mM sodium acetate (pH 5.0) over a CM5 chip that had been pre-activated with NHS/EDC (N-ethyl-N'[3-diethylamino)propyl]-carbodiimide), aiming at a surface density of >5000 resonance units (RU) corresponding to 100 fmols/$mm^2$. After coupling the sensor-chip was deactivated with 1 M ethanolamine. Binding of purified human uPAR as analyte was measured from 4 nM to 0.25 nM at using 10 mM HEPES, 150 mM NaCl, 3 mM EDTA (pH 7.4) containing (v/v) surfactant P20 as running buffer at a flow rate of 50 μl/min. In between cycles the sensor-chip was regenerated by two consecutive 10-μl injections of 0.1 M acetic acid/HCl (pH 2.5) in 0.5 M NaCl. The inhibition of 3-fold dilutions of the compounds in question was measured for 4 nM uPAR with identical running conditions. All experiments were performed on a BiacoreT200 instrument.

Results

For each inhibition peptide inhibition profile of uPAR binding to immobilized uPA there has been run a preceding standard curve and all calculations are based on the that standard curve. Table 1 summarizes the results.

TABLE 1

| | Sequence | $IC_{50}$ uPAR wt | $IC_{50}$ UPAR H47C-N259C |
|---|---|---|---|
| AE105 | DChaFsrYLWS-OH | 7.8 ± 1.0 nM | 4.5 ± 1.5 μM |
| AE344 | EE-O2Oc-O2Oc-DChaFsrYLWS-OH | 5.7 ± 0.5 nM | — |
| AE345 | EE-O2Oc-O2Oc-DChaFsrYLWS-$NH_2$ | 31.8 ± 1.5 nM | — |
| AE346 | O2Oc-O2Oc-DChaFsrYLWS-OH | 16.1 ± 0.9 nM | — |
| AE347 | EE-O2Oc-DChaFsrYLWS-$NH_2$ | 3.5 ± 0.1 nM | — |
| AE348 | E-O2Oc-DChaFsrYLWS-$NH_2$ | 6.7 ± 0.2 nM | — |
| AE349 | EE-DChaFsrYLWS-OH | 12.5 ± 0.6 nM | — |

It is clear from table 1 that a second generation of uPAR targeting peptides have been generated by expanding the hydrophilic linker region, a product with much better solubility properties has been obtained. Also this should be considered when comparing the present invention with the mentioned prior art documents mentioned above. This shows the effect provided by the present invention, which in turn is linked to the property of enhanced binding which is possible according to the present invention.

Moreover, in the enclosed sequence listing, sequences from table 1 are provided.

Based on the above, according to one embodiment of the present invention the peptide binding to uPAR has a sequence chosen from any of the following:

AE344: EE-O2Oc-O2Oc-DChaFsrYLWS-OH;
AE345: EE-O2Oc-O2Oc-DChaFsrYLWS-$NH_2$;
AE346: O2Oc-O2Oc-DChaFsrYLWS-OH;
AE347: EE-O2Oc-DChaFsrYLWS-$NH_2$;
AE348: E-O2Oc-DChaFsrYLWS-$NH_2$;
AE349: EE-DChaFsrYLWS-OH.

As mentioned, according to one embodiment of the present invention is of great interest to include a linker group comprising oligoethylene glycols which are connected by covalent bonds to at least one amino acid. In line with this and the above, according to one embodiment of the present invention, the peptide binding to uPAR has a sequence chosen from any of the following:

AE344: EE-O2Oc-O2Oc-DChaFsrYLWS-OH;
AE345: EE-O2Oc-O2Oc-DChaFsrYLWS-$NH_2$;
AE346: O2Oc-O2Oc-DChaFsrYLWS-OH;
AE347: EE-O2Oc-DChaFsrYLWS-$NH_2$;
AE348: E-O2Oc-DChaFsrYLWS-$NH_2$.

According to yet another specific embodiment, the peptide binding to uPAR has a sequence chosen from any of:

AE344: EE-O2Oc-O2Oc-DChaFsrYLWS-OH;
AE347: EE-O2Oc-DChaFsrYLWS-$NH_2$;
AE348: E-O2Oc-DChaFsrYLWS-$NH_2$;

These sequences, i.e. AE344, AE347 and AE348, provide for an enhanced binding property according to the present invention.

Moreover, also certain combinations of radionucleotides with the sequences mentioned above are of special interest according to the present invention. Therefore, according to one embodiment of the present invention, the radionuclide is for PET imaging and chosen from any of the following isotopes: 11C, 18F, 13N, 15O, 44Sc, 52gMn, 60Cu, 61Cu, 62Cu, 64Cu, 68Ga, 76Br, 82Rb, 86Y, 89Zr, 94mTc, 124I, preferably selected from any of 18F, 64Cu, 68Ga, 89Zr,
and wherein the peptide binding to uPAR has a sequence chosen from any of the following:

AE344: EE-O2Oc-O2Oc-DChaFsrYLWS-OH;
AE345: EE-O2Oc-O2Oc-DChaFsrYLWS-$NH_2$;
AE346: O2Oc-O2Oc-DChaFsrYLWS-OH;
AE347: EE-O2Oc-DChaFsrYLWS-$NH_2$;
AE348: E-O2Oc-DChaFsrYLWS-$NH_2$;
AE349: EE-DChaFsrYLWS-OH.

Furthermore, according to one embodiment of the present invention, the radionuclide is for SPECT imaging and chosen from any of the following isotopes: 67Ga, 111In, 123I, 125I, 131I, 99mTc, preferably selected from 99mTc, 111In, 123I,
and wherein the peptide binding to uPAR has a sequence chosen from any of the following:

AE344: EE-O2Oc-O2Oc-DChaFsrYLWS-OH;
AE345: EE-O2Oc-O2Oc-DChaFsrYLWS-$NH_2$;
AE346: O2Oc-O2Oc-DChaFsrYLWS-OH;
AE347: EE-O2Oc-DChaFsrYLWS-$NH_2$;
AE348: E-O2Oc-DChaFsrYLWS-$NH_2$;
AE349: EE-DChaFsrYLWS-OH.

In addition, according to yet another embodiment, the radionuclide is for targeted radionuclide therapy (alpha, beta-emitters or auger) and is selected from any of the following isotopes: 67Cu, 177Lu, 89Sr, 90Y, 117mSn, 131I, 153Sm, 166Ho, 186Re, 188Re, 211At, 212Pb, 212Bi, 213Bi, 223Ra, 224Ra, 225Ac, 227Th, preferably selected from 67Cu, 90Y, 177Lu, 211At, 225Ac, 227Th,
and wherein the peptide binding to uPAR has a sequence chosen from any of the following:

AE344: EE-O2Oc-O2Oc-DChaFsrYLWS-OH;
AE345: EE-O2Oc-O2Oc-DChaFsrYLWS-$NH_2$;
AE346: O2Oc-O2Oc-DChaFsrYLWS-OH;
AE347: EE-O2Oc-DChaFsrYLWS-$NH_2$;
AE348: E-O2Oc-DChaFsrYLWS-$NH_2$;
AE349: EE-DChaFsrYLWS-OH.

Also in all three different cases above, AE344-AE348 are often preferred alternatives. Furthermore, AE344 is of special interest according to the present invention.

In line with the above, according to one preferred embodiment of the present invention, the peptide binding to uPAR has a sequence being AE344: EE-O2Oc-O2Oc-DChaFsrYLWS-OH.

In table 2 there is provided the in vivo tumor retention in U87MG human xenograft glioblastoma tumors implanted subcutaneously. As notable for $^{177}$ Lu-NOTA-AE344, the tumor uptake (both 0.5 h and 2 h post injection) is considerably greater than for $^{177}$Lu-DOTA-AE105. It should, however, be noted that the best type of combination of radionuclide, chelating agent and peptide sequence for different types of technical applications is not simple to set and provide. This may, e.g. be seen when comparing $^{64}$ Cu-DOTA-AE105 and $^{64}$ Cu-NOTA-AE344 where $^{64}$ Cu-DOTA-AE105 shows a greater tumor uptake than $^{64}$Cu-NOTA-AE344, which thus provides a different result direction in comparison to the $^{177}$Lu comparison mentioned above.

TABLE 2

| Compound | Tumor uptake 0.5 h post injection (% ID/g) | Tumor uptake 2 h post injection (% ID/g) |
|---|---|---|
| $^{177}$Lu-DOTA-AE105 | 0.96 | 0.23 |
| $^{177}$Lu-NOTA-AE344 | 3.53 | 0.61 |
| $^{64}$Cu-DOTA-AE105 | 2.3 | 2.6 |
| $^{64}$Cu-NOTA-AE344 | 0.7 | 0.36 |

As may be noted, to include DOTA or NOTA in the uPAR-targeting peptide conjugate may be of interest according to the present invention. Based on this, according to one embodiment of the present invention, DOTA or NOTA is included in the uPAR-targeting peptide conjugate.

Moreover, with reference to the data provided above, according to one embodiment of the present invention, the uPAR targeting peptide conjugate is $^{177}$Lu-NOTA-AE344 or $^{64}$Cu-NOTA-AE344. Also DOTA versions are of interest according to the present invention. Therefore, according to yet another embodiment, the uPAR targeting peptide conjugate is $^{177}$Lu-DOTA-AE344 or $^{64}$Cu-DOTA-AE344.

Figure 1:
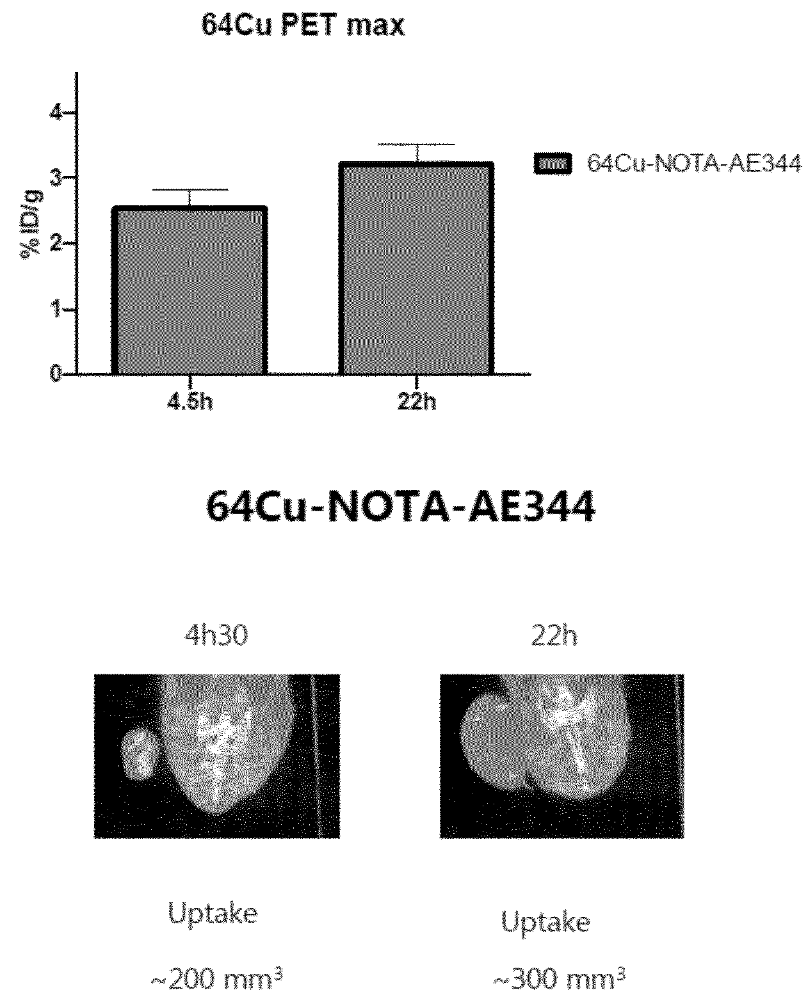
In FIG. 1 there is provided a radionucleotide labeled version of AE344 according to the present invention, in this case $^{64}$Cu-NOTA-AE344, which thus is a uPAR-targeting peptide conjugate according to one specific embodiment of the present invention. The figure shows the uptake in tumors of this compound alternative according to the present invention.
Figure 2:
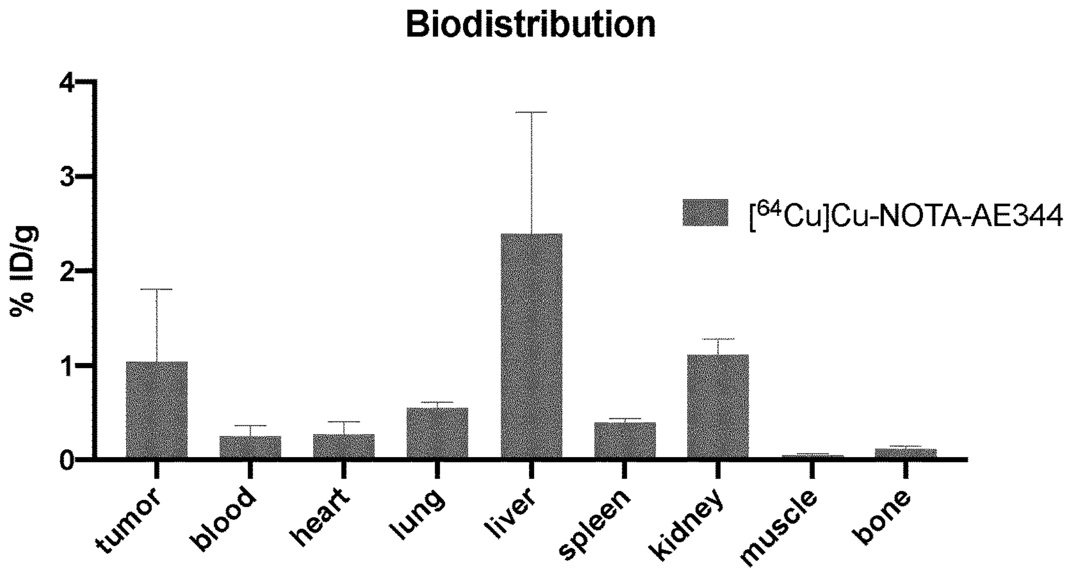

Moreover, in FIG. 2 there is shown the $^{64}$Cu-NOTA-AE344 biodistribution data.

The invention claimed is:

1. A urokinase Plasminogen Activator Receptor targeting peptide conjugate comprising:

a radionuclide coupled via a chelating agent or covalently coupled to a peptide binding to the urokinase Plasminogen Activator Receptor; and a linker group, wherein the peptide binding to the urokinase Plasminogen Activator Receptor and the linker group is connected by a covalent bond, wherein the linker group comprises an oligo-ethylene glycol, an oligo-glycerol, an oligo-lactic acid, a carbohydrate, an oligo-ethylene glycol connected by a covalent bond to at least one amino acid, an oligo-glycerol connected by a covalent bond to at least one amino acid, an oligo-lactic acid connected by a covalent bond to at least one amino acid, or a carbohydrate connected by a covalent bond to at least one amino acid, and wherein the peptide binding to the urokinase Plasminogen Activator Receptor has a sequence chosen from:

AE344: EE-O2Oc-O2Oc-DChaFsrYLWS-OH;

AE345: EE-O2Oc-O2Oc-DChaFsrYLWS-$NH_2$;

AE346: O2Oc-O2Oc-DChaFsrYLWS-OH;

AE347: EE-O2Oc-DChaFsrYLWS-$NH_2$;

AE348: E-O2Oc-DChaFsrYLWS-$NH_2$; or

AE349: EE-DChaFsrYLWS-OH.

2. The urokinase Plasminogen Activator Receptor-targeting peptide conjugate according to claim 1, wherein the linker group comprises the oligoethylene glycol connected by a covalent bond to at least one amino acid.

3. The urokinase Plasminogen Activator Receptor-targeting peptide conjugate according to claim 1, wherein the at least one amino acid is selected from proteinogenic amino acids, non-proteinogenic amino acids, natural amino acids, and synthetic amino acids.

4. The urokinase Plasminogen Activator Receptor-targeting peptide conjugate according to claim 1, wherein the at least one amino acid includes a C-alpha alkylated amino acid, an N-alkylated amino acid, or a naturally occurring beta-amino acid.

5. The urokinase Plasminogen Activator Receptor-targeting peptide conjugate according to claim 1, wherein the at least one amino acid includes an amino acid with a non-proteinogenic side-chain.

6. The urokinase Plasminogen Activator Receptor-targeting peptide conjugate according to claim 1, wherein the linker group is -Glu-Glu-NH—$CH_2$—$CH_2$—O—$CH_2$—$CH_2$—O—$CH_2$—CO—NH—$CH_2$—$CH_2$—O—$CH_2$—$CH_2$—O—$CH_2$—CO—.

7. The urokinase Plasminogen Activator Receptor-targeting peptide conjugate according to claim 1, wherein the radionuclide is for PET imaging, and is selected from the group consisting of: $^{11}C$, $^{18}F$, $^{13}N$, $^{15}O$, $^{44}Sc$, $^{52g}Mn$, $^{60}Cu$, $^{61}Cu$, $^{62}Cu$, $^{64}Cu$, $^{68}Ga$, $^{76}Br$, $^{82}Rb$, $^{86}Y$, $^{89}Zr$, $^{94m}Tc$, and $^{124}I$.

8. The urokinase Plasminogen Activator Receptor-targeting peptide conjugate according to claim 1, wherein the radionuclide is for SPECT imaging and is selected from the group consisting of: $^{67}Ga$, $^{111}In$, $^{123}I$, $^{125}I$, $^{131}I$, and $^{99m}Tc$.

9. The urokinase Plasminogen Activator Receptor-targeting peptide conjugate according to claim 1, wherein the radionuclide is for targeted radionuclide therapy comprising alpha emitters, beta-emitters, or auger electron emitters, and is selected from the group consisting of: $^{67}Cu$, $^{177}Lu$, $^{89}Sr$, $^{90}Y$, $^{117m}Sn$, $^{131}I$, $^{153}Sm$, $^{166}Ho$, $^{186}Re$, $^{188}Re$, $^{211}At$, $^{212}Pb$, $^{212}Bi$, $^{213}Bi$, $^{223}Ra$, $^{224}Ra$, $^{225}Ac$, and $^{227}Th$.

10. The urokinase Plasminogen Activator Receptor-targeting peptide conjugate according to claim 1, wherein the receptor binding peptide is selected from the group consisting of:

-Asp-Cha-Phe-ser-arg-Tyr-Leu-Trp-Ser; and

-Asp-Cha-Phe-ser-arg-Tyr-Leu-Trp-Ser-$NH_2$.

11. The urokinase Plasminogen Activator Receptor-targeting peptide conjugate according to claim 1, wherein the urokinase Plasminogen Activator Receptor and the linker group is connected by a covalent bond selected from the group consisting of: an amide, a carbamate, a thiourea, an ester, an ether, an amine, and a triazole.

12. The urokinase Plasminogen Activator Receptor-targeting peptide conjugate according to claim 1, wherein the uPAR-binding affinity is less than 100 nM.

13. The urokinase Plasminogen Activator Receptor-targeting peptide conjugate according to claim 1, wherein the chelating agent is selected from the group consisting of: DOTA, CB-DO2A, 3p-C-DEPA, TCMC, Oxo-DO3A, TETA, TE2A, CB-TE2A, CB-TE1A1P, CB-TE2P, MM-TE2A, DM-TE2A, SarAr, SarAr-NCS, diamSar, AmBaSar, BaBaSar, ATSM, CB-TE1A1P and CB-TE2P, NOTA, NETA, TACN-TM, NODAGA, TRAP, AAZTA, DATA, $H_2$dedpa, CP256, PCTA, THP, DTPA, 1B4M-DTPA, CHX-A"-DTPA, TRAP-PRP9, NOPO, DFO HOPO, H6phospa, PCTA, $H_2$dedpa, $H_4$octapa, $H_2$azapa, $H_5$decapa, HBED, HBED-cc, SHBED, BPCA, CP256, HEHA, PEPA and RESCA1.

14. The urokinase Plasminogen Activator Receptor-targeting peptide conjugate according to claim 1, wherein the peptide binding to the urokinase Plasminogen Activator Receptor has a sequence selected from the group consisting of:

AE344: EE-O2Oc-O2Oc-DChaFsrYLWS-OH;

AE345: EE-O2Oc-O2Oc-DChaFsrYLWS-$NH_2$;

AE346: O2Oc-O2Oc-DChaFsrYLWS-OH;

AE347: EE-O2Oc-DChaFsrYLWS-$NH_2$; and

AE348: E-O2Oc-DChaFsrYLWS-$NH_2$.

15. The urokinase Plasminogen Activator Receptor-targeting peptide conjugate according to claim 1, wherein the peptide binding to the urokinase Plasminogen Activator Receptor has a sequence selected from the group consisting of:

AE344: EE-O2Oc-O2Oc-DChaFsrYLWS-OH;

AE347: EE-O2Oc-DChaFsrYLWS-$NH_2$; and

AE348: E-O2Oc-DChaFsrYLWS-$NH_2$.

16. The urokinase Plasminogen Activator Receptor-targeting peptide conjugate according to claim 1, wherein the radionuclide is for PET imaging and is selected from the group consisting of $^{18}F$, $^{64}Cu$, $^{68}Ga$, and $^{89}Zr$.

17. The urokinase Plasminogen Activator Receptor-targeting peptide conjugate according to claim 1, wherein the radionuclide is for SPECT imaging and is selected from the group consisting of: $^{99m}Tc$, $^{111}In$, and $^{123}I$.

18. The urokinase Plasminogen Activator Receptor-targeting peptide conjugate according to claim 1, wherein the radionuclide is for targeted radionuclide therapy comprising alpha emitters, beta-emitters, or auger electron emitters, and is selected from the group consisting of: $^{67}Cu$, $^{90}Y$, $^{177}Lu$, $^{211}At$, $^{212}Pb$, $^{225}Ac$, and $^{227}Th$.

19. The urokinase Plasminogen Activator Receptor-targeting peptide conjugate according to claim 1, wherein DOTA or NOTA is included in the uPAR-targeting peptide conjugate.

20. The urokinase Plasminogen Activator Receptor-targeting peptide conjugate according to claim 1, wherein the peptide binding to the urokinase Plasminogen Activator Receptor has a sequence being AE344: EE-O2Oc-O2Oc-DChaFsrYLWS-OH.

21. The urokinase Plasminogen Activator Receptor-targeting peptide conjugate according to claim 1, wherein the urokinase Plasminogen Activator Receptor targeting peptide conjugate is $^{177}$Lu-NOTA-AE344 or $^{64}$Cu-NOTA-AE344.

22. The urokinase Plasminogen Activator Receptor-targeting peptide conjugate according to claim 1, wherein the urokinase Plasminogen Activator Receptor targeting peptide conjugate is $^{177}$Lu-DOTA-AE344 or $^{64}$Cu-DOTA-AE344.

23. A method involving using a urokinase Plasminogen Activator Receptor-targeting peptide conjugate according to claim 1 in the treatment of a disease or in diagnosis of a disease.

24. The method according to claim 23, wherein the urokinase Plasminogen Activator Receptor-targeting peptide conjugate is included in a pharmaceutical composition.

25. The method according to claim 24, wherein the disease is a cancer selected from the group consisting of: gliomas, glioblastomas, a cancerous brain tumor, pancreatic cancer, oropharyngeal cancer, head-and-neck cancer, breast cancer, lung cancer, colorectal cancer, esophageal cancer, gastric cancer, liver cancer, a neuroendocrine tumor, a neuroendocrine carcinoma, and prostate cancer.

26. The method according to claim 24, wherein the disease is an inflammatory disease selected from the group consisting of: arthritis and atherosclerosis.

27. The urokinase Plasminogen Activator Receptor-targeting peptide conjugate according to claim 1, wherein the at least one amino acid includes aminoisobutyric acid, sarcosine, or beta-alanine.

28. The urokinase Plasminogen Activator Receptor-targeting peptide conjugate according to claim 1, wherein the at least one amino acid includes an amino acids having a non-proteinogenic side-chain comprising cyclohexyl alanine, a gamma-amino acid, or a dipeptide mimic.

29. The urokinase Plasminogen Activator Receptor-targeting peptide conjugate according to claim 1, wherein the radionuclide is selected from the group consisting of: $^{18}F$, $^{64}Cu$, $^{68}Ga$, and $^{89}Zr$.

30. The urokinase Plasminogen Activator Receptor-targeting peptide conjugate according to claim 1, wherein the radionuclide is selected from the group consisting of: $^{99m}Tc$ $^{111}In$, and $^{123}I$.

31. The urokinase Plasminogen Activator Receptor-targeting peptide conjugate according to claim 1, wherein the radionuclide is for targeted radionuclide therapy comprising alpha emitters, beta-emitters, or auger electron emitters, and is selected from the group consisting of: $^{67}Cu$, $^{90}Y$, $^{177}Lu$, $^{211}At$, $^{212}Pb$, $^{225}Ac$, and $^{227}Th$.

32. The urokinase Plasminogen Activator Receptor-targeting peptide conjugate according to claim 1, wherein the chelating agent is selected from the group consisting of: DOTA, NOTA, CB-TE2A, NODAGA, DFO, HBED, and HBED-cc.

33. A method involving using a urokinase Plasminogen Activator Receptor-targeting peptide conjugate according to claim 1 in the treatment of cancer or an inflammatory disease.

* * * * *